United States Patent
Xu

(10) Patent No.: US 9,850,244 B2
(45) Date of Patent: Dec. 26, 2017

(54) METHOD FOR PREPARING PALBOCICLIB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/595,167

(22) Filed: May 15, 2017

(65) Prior Publication Data

US 2017/0247379 A1 Aug. 31, 2017

Related U.S. Application Data

(63) Continuation of application No. PCT/CN2015/089737, filed on Sep. 16, 2015.

(30) Foreign Application Priority Data

Nov. 26, 2014 (CN) .......................... 2014 1 0691233

(51) Int. Cl.
| | |
|---|---|
| C07D 471/04 | (2006.01) |
| A61K 31/535 | (2006.01) |
| A61K 31/5395 | (2006.01) |
| C07B 43/04 | (2006.01) |
| C08K 5/03 | (2006.01) |
| C08K 5/34 | (2006.01) |
| C08K 5/3432 | (2006.01) |

(52) U.S. Cl.
CPC .......... *C07D 471/04* (2013.01); *A61K 31/535* (2013.01); *A61K 31/5395* (2013.01); *C07B 43/04* (2013.01); *C08K 5/03* (2013.01); *C08K 5/34* (2013.01); *C08K 5/3432* (2013.01)

(58) Field of Classification Search
CPC .................................................. C07D 471/04

USPC ......................................................... 544/279
See application file for complete search history.

(56) References Cited

FOREIGN PATENT DOCUMENTS

| | | |
|---|---|---|
| CN | 101001857 A | 7/2007 |
| CN | 101511829 A | 8/2009 |
| CN | 103501789 A | 1/2014 |
| CN | 104447743 A | 3/2015 |
| WO | 2003062236 A1 | 7/2003 |
| WO | 2008032157 A2 | 3/2008 |
| WO | 2012018540 A1 | 2/2012 |
| WO | 2012068381 A2 | 5/2012 |

OTHER PUBLICATIONS

Toogood L. Peter, et al. "Discovery of a Potent and Selective Inhibitor of Cyclin-Dependent 1-10 Kinase 4/6" Journal of Medicinal Chemistry, vol. 48, No. 7, Mar. 2, 2005 (Mar. 2, 2005) ISSN: Web Edition ISSN:1520-4804, p. 2399.

*Primary Examiner* — Jeffrey H Murray
(74) *Attorney, Agent, or Firm* — Perkins Coie LLP

(57) ABSTRACT

The invention discloses a method for preparing Palbociclib (I). The preparation method comprises the steps of: causing a ring-closing reaction of 2-acetyl-2-butenoic acid methyl ester and malononitrile to occur in an alkaline condition to generate 1,4,5,6-tetrahydro-2-methoxyl-4-methyl-5-acetyl-6-oxy-3-pyridine carbonitrile (II); causing a substitution reaction of the intermediate(II) and halogenated cyclopentane(III) to occur under the effect of acid binding agent to generate N-cyclopentyl-1,4,5,6-tetrahydro-2-methoxyl-4-methyl-5-acetyl-6-oxy-3-pyridinecarbonitrile (IV); causing a condensation reaction of the intermediate(IV) and N-[5-(1-piperazinyl)-2-pyridinyl]guanidine (V) to occur to generate 6-acetyl-8-cyclopentyl-5,8-dihydro-5-methyl-2-[[5-(1-piperazinyl)-2-pyridinyl]amino]-pyrido[2,3-d]pyrimidin-7 (6H)-one (VI); and causing a dehydrogenation reaction of the intermediate(VI) and sodium selenate to occur to prepare Palbociclib(I).The preparation method has readily available raw materials and a simple process, is economical and environmentally friendly, and is suitable for industrial production.

10 Claims, No Drawings

METHOD FOR PREPARING PALBOCICLIB

CROSS REFERENCE TO RELATED APPLICATIONS

This application is a continuation of International Application No. PCT/CN2015/089737 filed Sep. 16, 2015, which claims priority to CN 2014106912330 filed Nov. 26, 2014, both of which are incorporated herein by reference.

TECHNOLOGY FIELD

This invention belongs to the technology field of organic synthetic route design and preparation of its active pharmaceutical ingredients and intermediates, which particularly relates to the preparation method of a drug which may be used for treatment of breast cancer, Palbociclib.

BACKGROUND ART

Palbociclib is a cyclin-dependent kinase (CDK4/6) inhibitor developed by Pfizer Inc. It obtained the qualification of "breakthrough therapy" from the U.S. FDA in April 2013. Because of its good clinical performance in Phase III, in August 2014, Pfizer Inc. submitted an application for going on sale to the U.S. FDA and obtained the prioritized examination qualification, and used it for first-line treatment of advanced breast cancer of estrogen receptor positive (ER+) and human epidermal growth factor receptor 2 negative (HER2−). Successful research of this drug will provide another important choice for the patients with metastatic breast cancer. As this drug still has no standard translated name in Chinese, the applicant hereby transliterates it to "帕博西尼".

The chemical name of Palbociclib (I) is: 6-acetyl-8-cyclopentyl-5-methyl-2-[[5 -(1-piperazinyl)-2-pyridinyl]amino]-pyrido[2,3-d]pyrimidin-7 (8H)-one, and its structural formula is:

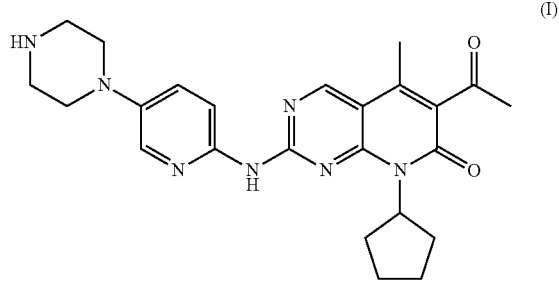

Palbociclib

The PCT patents WO2003062236, WO2008032157, WO2012018540 and WO2012068381 of the original research & development Company as well as documents such as Page 2388-2406, Vol. 48, *J. Med. Chem.,* 2005 all have reported the synthetic methods of Palbociclib. Its preparation mainly has two synthetic routes.

The first route:

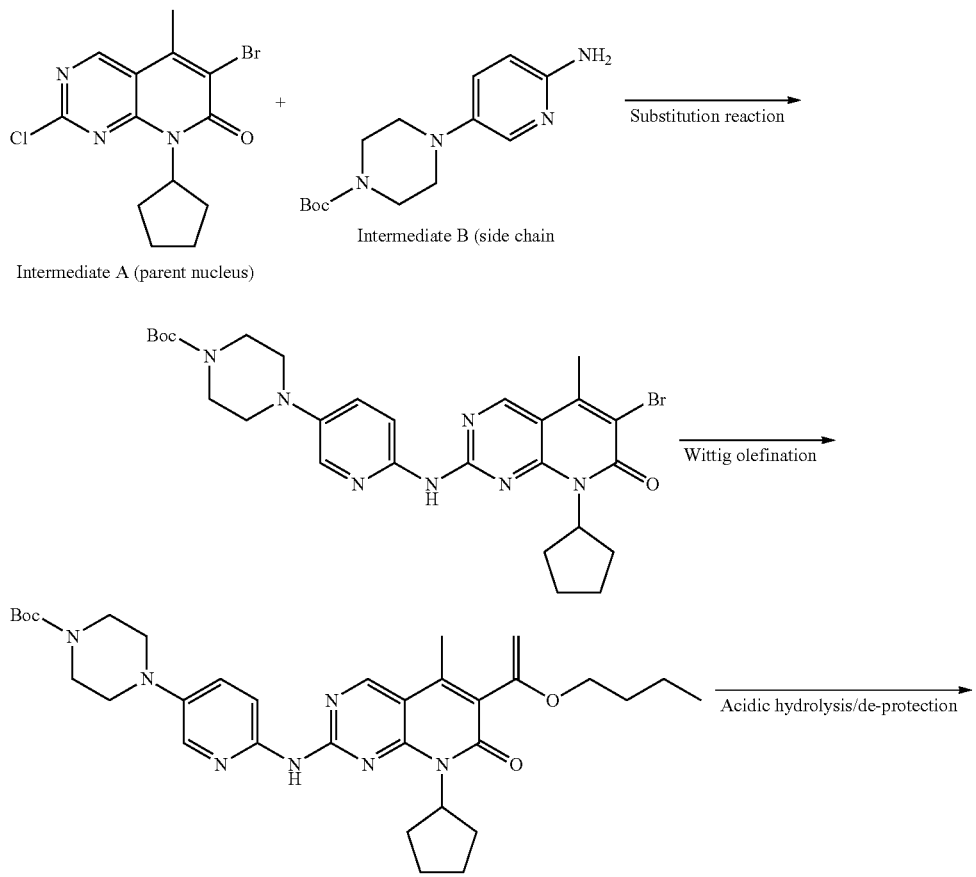

Intermediate A (parent nucleus)

Intermediate B (side chain)

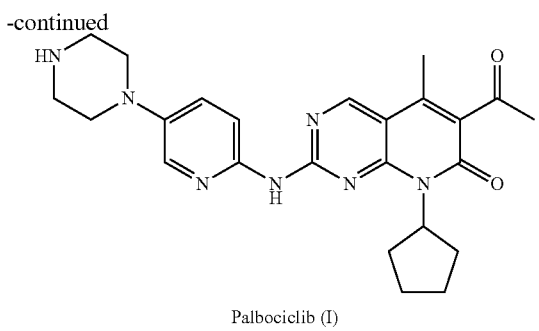
Palbociclib (I)
The first route takes intermediate A (parent nucleus) and intermediate B (side chain) as the raw materials, and obtains Palbociclib (I) through the reactions such as substitution reaction, Wittig olefination, acid hydrolysis (rearrangement) and de-protection.
The second route:
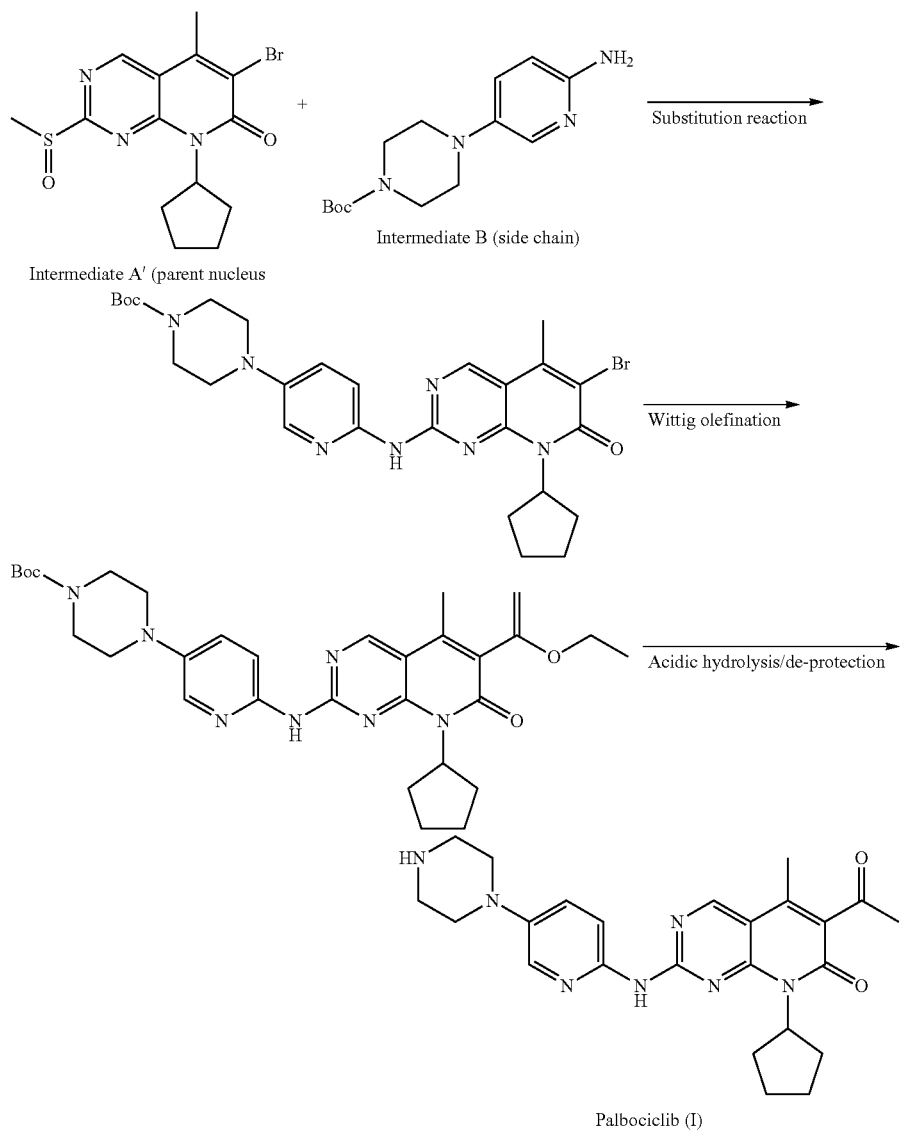
Palbociclib (I)

The second route obtains Palbociclib (I) through the reactions of the changed intermediate A' (parent nucleus) and intermediate B (side chain) and then through 6-position modification and de-protection.

Through analysis of the above two synthetic routes, the main difference between them is the difference in 2-position substituent groups of intermediates A and A' (parent nucleus). The intermediate A in Route 1 is 2-halogen (chlorine), and the intermediate A' in Route 2 is 2-methylsulfinyl group; obviously, the selective difference between 2-methylsulfinyl group and 6-halogen (bromine) in the intermediate A' is greater than the selective difference between two halogens (chlorine and bromine) in the intermediate A, so the synthesis design in Route 2 avoids a competitive side reaction caused due to two halogens with similar reactivity in Route 1, and greatly improves reaction yield and product purity. However, synthesis of the core intermediates A and A' (parent nucleus) is relatively complex no matter for Route 1 or Route 2. Its main raw materials 2,5,6-trisubstituted pyrimidine rings are hard to come by, and there are disadvantages such as various reaction steps and complex side reactions, which greatly limits industrial production of this drug.

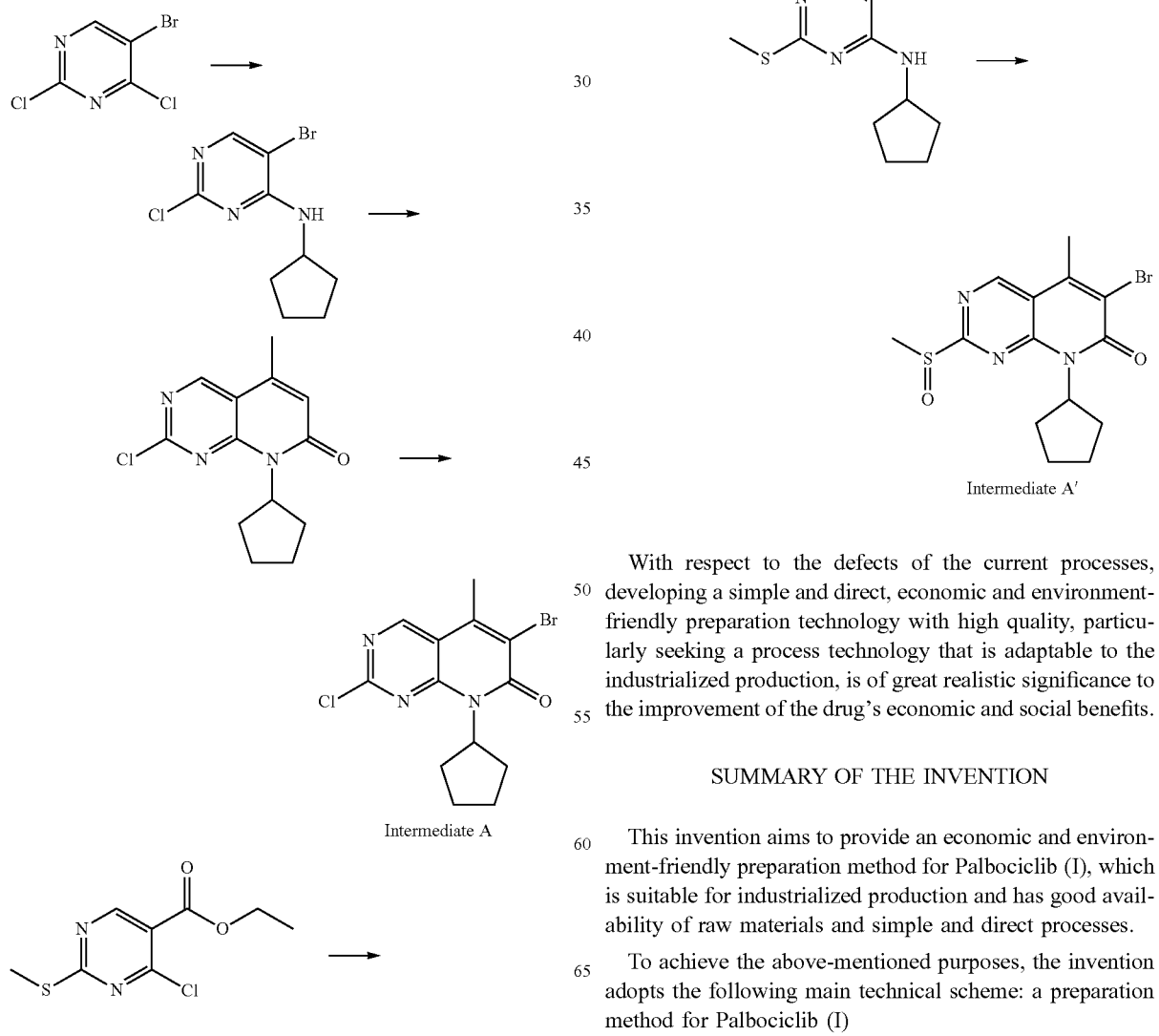

Intermediate A

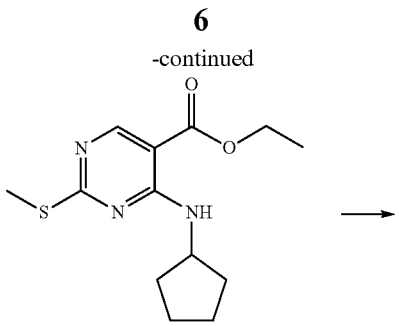

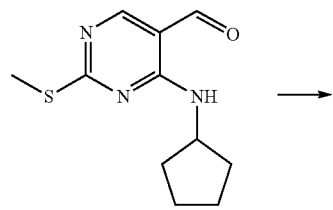

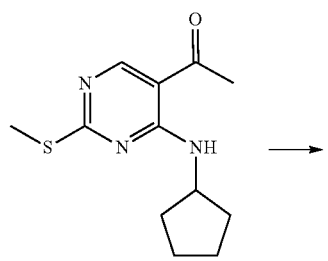

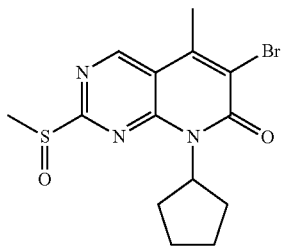

Intermediate A'

With respect to the defects of the current processes, developing a simple and direct, economic and environment-friendly preparation technology with high quality, particularly seeking a process technology that is adaptable to the industrialized production, is of great realistic significance to the improvement of the drug's economic and social benefits.

SUMMARY OF THE INVENTION

This invention aims to provide an economic and environment-friendly preparation method for Palbociclib (I), which is suitable for industrialized production and has good availability of raw materials and simple and direct processes.

To achieve the above-mentioned purposes, the invention adopts the following main technical scheme: a preparation method for Palbociclib (I)

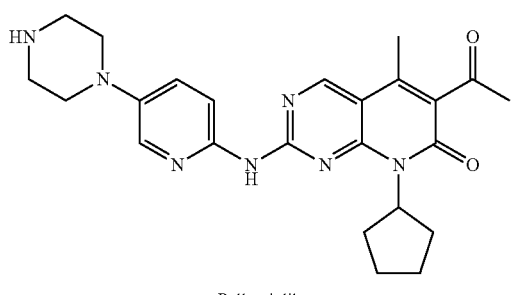

Palbociclib

The preparation method comprises the steps of: causing a ring-closing reaction of 2-acetyl-2-butenoic acid methyl ester and malononitrile to occur in an alkaline condition to generate 1,4,5,6-tetrahydro-2-methoxyl-4-methyl-5-acetyl-6-oxy-3-pyridine carbonitrile (II); causing a substitution reaction of 1,4,5,6-tetrahydro-2-methoxyl-4-methyl-5-acetyl-6-oxy-3-pyridine carbonitrile (II) and halogenated cyclopentane (III) to occur under the effect of acid binding agent to generate N-cyclopentyl-1,4,5,6-tetrahydro-2-methoxyl-4-methyl-5-acetyl-6-oxy-3-pyridine carbonitrile (IV); causing a condensation reaction of N-cyclopentyl-1,4,5,6-tetrahydro-2-methoxyl-4-methyl-5-acetyl-6-oxy-3-pyridinecarbonitrile (IV) and N-[5-(1-piperazinyl)-2-pyridinyl]guanidine (V) to occur to generate 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI); and causing a dehydrogenation reaction of 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI) and sodium selenate to occur to prepare Palbociclib (I).

Additionally, this invention has also proposed auxiliary technical schemes as follows:

Molar ratio of the aforesaid ring-closing reaction of 2-acetyl-2-butenoic acid methyl ester and malononitrile is 1:0.5-1.5, and 1:1.2-1.4 is preferred.

Alkali required for the aforesaid ring-closing reaction of 2-acetyl-2-butenoic acid methyl ester and malononitrile is potassium hydroxide, sodium hydroxide, sodium methoxide, sodium ethoxide, potassium tert-butoxide, sodium tert-butoxide or sodium hydride, and sodium methoxide or sodium hydride is preferred.

Solvent of the aforesaid ring-closing reaction of 2-acetyl-2-butenoic acid methyl ester and malononitrile is methanol, ethyl alcohol, isopropyl alcohol or ethylene glycol, and methanol is preferred.

Temperature of the aforesaid ring-closing reaction of 2-acetyl-2-butenoic acid methyl ester and malononitrile is 0-100° C., and 25-75° C. is preferred.

Halogen in the raw material halogenated cyclopentane (III) in the aforesaid substitution reaction is fluorine, chlorine, bromine or iodine, and bromine or iodine is preferred.

The acid binding agent of the aforesaid substitution reaction of 1,4,5,6-tetrahydro-2-methoxyl-4-methyl-5-acetyl-6-oxy-3-pyridine carbonitrile (II) and halogenated cyclopentane (III) is triethylamine, pyridine, N-methylmorpholine, diisopropylethylamine, 4-dimethylamino-pyridine, potassium carbonate, lithium carbonate, potassium tert-butoxide or sodium hydride, and potassium tert-butoxide or sodium hydride is preferred.

Solvent of the aforesaid substitution reaction of 1,4,5,6-tetrahydro-2-methoxyl-4-methyl-5-acetyl-6-oxy-3-pyridine carbonitrile (II) and halogenated cyclopentane (III) is dichloromethane, chloroform, 1,2-dichloroethane, acetonitrile, methylbenzene, tetrahydrofuran, dimethyl carbonate or dioxane, and dichloromethane or tetrahydrofuran is preferred.

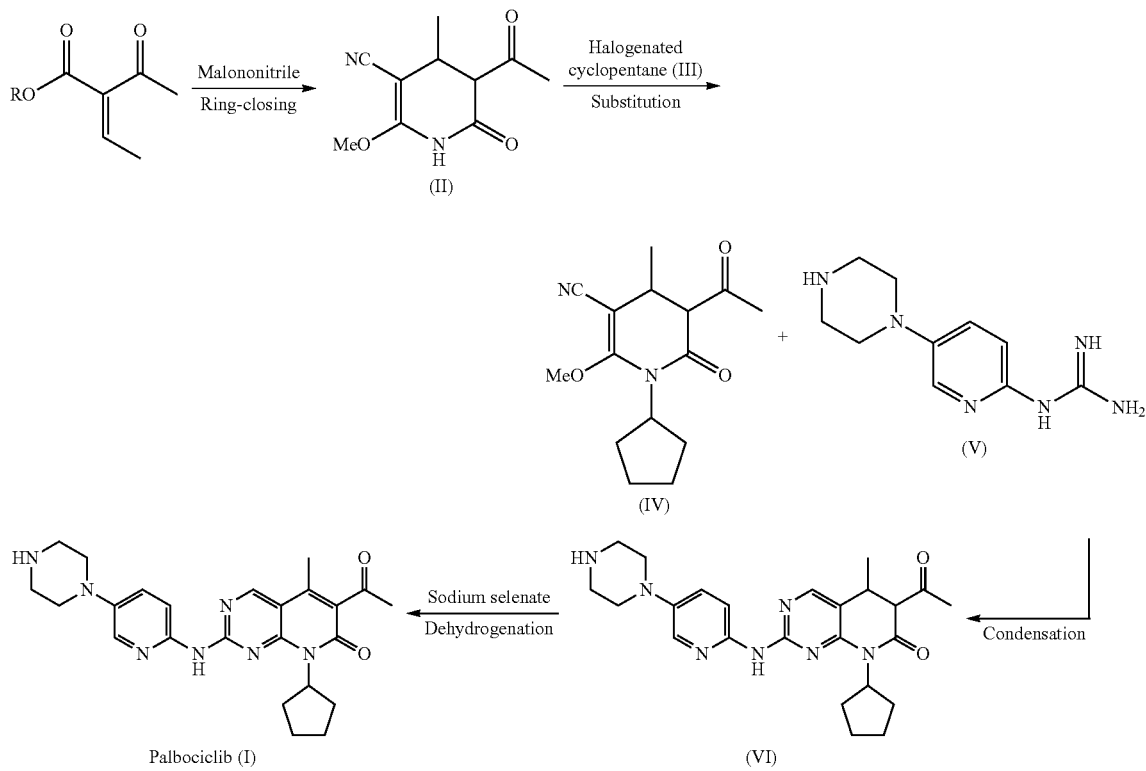

Molar ratio of the aforesaid condensation reaction of N-cyclopentyl-1,4,5,6-tetrahydro-2-methoxyl-4-methyl-5-acetyl-6-oxy-3-pyridinecarbonitrile (IV) and N-[5-(1-piperazinyl)-2-pyridinyl]guanidine (V) is 1:1.0-3.0, and 1:1.5-2.5 is preferred.

Solvent of the aforesaid condensation reaction of N-cyclopentyl-1,4,5,6-tetrahydro-2-methoxyl-4-methyl-5-acetyl-6-oxy-3-pyridinecarbonitrile (IV) and N-[5-(1-piperazinyl)-2-pyridinyl]guanidine (V) is methylbenzene, dimethylbenzene, acetic acid, N,N-dimethylformamide, N,N-dimethylacetamide or dimethylsulfoxide, and methylbenzene or dimethylbenzene is preferred.

Temperature of the aforesaid condensation reaction of N-cyclopentyl-1,4,5,6-tetrahydro-2-methoxyl-4-methyl-5-acetyl-6-oxy-3-pyridinecarbonitrile (IV) and N-[5-(1-piperazinyl)-2-pyridinyl]guanidine (V) is 50-150° C., and 90-120° C. is preferred.

Molar ratio of the aforesaid dehydrogenation reaction of 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI) and sodium selenate is 1:1.0-2.0, and 1:1.2-1.4 is preferred.

Solvent of the aforesaid dehydrogenation reaction of 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI) and sodium selenate is dimethylsulfoxide; the reaction temperature is 100-180° C., and 150-160° C. is preferred.

Compared to the existing technologies, the preparation method for Palbociclib (I) involved in this invention features good availability of raw materials, simple and direct processes and economy and environmental protection, which thus is beneficial to the industrialized production of the active pharmaceutical ingredients, and can promote its economic and technical development.

DETAILED DESCRIPTION OF THE PREFERRED EMBODIMENTS

A detailed and unrestricted description is further made as follows against the technical scheme of this invention in combination with several preferred embodiments.

Hereinto, for preparation of the raw materials including 2-acetyl-2-methylcrotonate and N-[5-(1-piperazinyl)-2-pyridinyl]guanidine (V), see "Tetrahedron, 58(3), 589-596; 2002" and in the patent WO2006095159 published on Sep. 14, 2006 and named "(IMIDAZOLO-5-YL)-2-ANILO-PYRIMIDINES AS AGENTS FOR THE INHIBITION OF CELL PROLIFERATION" respectively for their preparation methods of the same compounds.

Embodiment I

Add 2-acetyl-2-butenoic acid methyl ester (II) (7.1 g, 50 mmol) and 30 mL of methanol into the dry reaction flask, and add 30 mL of methanol solution with sodium methoxide (5.4 g, 100 mmol) drop by drop at room temperature, and conduct stirring reactions for 15 minutes after completing the addition. Add 20 mL of methanol solution with malononitrile (4.0 g, 60 mmol) drop by drop. Raise the temperature until the methanol flows back, continue the reaction for 4-5 hours, and complete TLC detection reaction. Reduce the pressure, recover the solvent, and dissolve the residue in water. Adjust the solvent's pH value to 8.0-9.0 with diluted hydrochloric acid in an ice bath, conduct extraction with dichloromethane for three times, and combine organic phases. After drying and concentration with anhydrous sodium sulfate, recrystallize the obtained residue with ethyl acetate and normal hexane (1:1, V/V), and dry it by vacuum to obtain 8.2 g of white solid 1,4,5,6-tetrahydro-2-methoxyl-4-methyl-5-acetyl-6-oxy-3-pyridine carbonitrile (III); yield rate is 78.8%; mass spectrum (EI): m/z 209 (M+H).

Embodiment II

Add 1,4,5,6-tetrahydro-2-methoxyl-4-methyl-5-acetyl-6-oxy-3-pyridine carbonitrile (III) (2.1 g, 10 mmol), 0.6 g of silicone oil containing 60% sodium hydride and 30 mL of N,N-dimethylformamide into the reaction flask, raise the temperature to 55° C., and conduct stirring reactions for 30 minutes. Reduce the temperature to room temperature, add Iodo-cyclopentane (2.9 g, 15 mmol), then raise the temperature to 55° C. again, and conduct stirring reactions for 30 minutes. Complete the TLC detection reaction. Conduct quenching reaction with water, conduct extraction with ethyl acetate for three times, and combine organic phases. After drying and concentration with anhydrous sodium sulfate, solids are separated out. Recrystallize the obtained crude product with normal hexane and ethyl acetate (2:1, V/V), and dry it by vacuum to obtain 2.1 g of off-white solid N-cyclopentyl-1,4,5,6-tetrahydro-2-methoxyl-4-methyl-5-acetyl-6-oxy-3-pyridinecarbonitrile (IV); yield rate is 76.1%; mass spectrum (EI): m/z 277 (M+H).

Embodiment III

Add N-cyclopentyl-1,4,5,6-tetrahydro-2-methoxyl-4-methyl-5-acetyl-6-oxy-3-pyridinecarbonitrile (IV) (2.8 g, 10 mmol), N-[5-(1-piperazinyl)-2-pyridinyl]guanidine (V) (4.4 g, 20 mmol) and 15 mL of dimethylbenzene into the reaction flask in the nitrogenous atmosphere; raise the temperature to 150° C., conduct stirring reactions for 18-20 hours, and complete TLC detection reaction. Reduce the pressure, distill off the solvent, reduce the temperature to room temperature, add methanol, and then solids are separated out. For filtration, clean the filter cake twice with cold methanol, and then dry it to obtain 2.56 g of off-white solid 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI); yield rate is 58.2%; mass spectrum (EI): m/z 450 (M+H).

Embodiment IV

Add 6-acetyl-8-cyclopentyl-5,8-dihydro-5-methyl-2-[[5-(1-piperazinyl)-2-pyridinyl]amino]-pyrido[2,3-d]pyrimidin-7(6H)-one (VI) (2.25 g, 5 mmol), sodium selenate (1.04 g, 6 mmol) and 20 mL of dimethylsulfoxide (DMSO) into the reaction flask, raise the temperature to 150-160° C., and conduct stirring reactions for 5-6 hours. Reduce the temperature to room temperature, add 200 mL of water, and then solids are separated out. For filtration, clean the filter cake successively with ethyl alcohol and diethyl ether, and then obtain 2.1 g of white solid Palbociclib (I); yield rate is 94.0%; mass spectrum (EI): m/z 448 (M+H).

It needs to be noted that the above-mentioned embodiments are only used to describe the technical thought and characteristics of the invention and the purposes are to get the persons familiar with this technology understand the contents of the invention and implement the invention accordingly. They shall not be used to restrict the protection scope of this invention. All equivalent changes or modifications made upon the spiritual essence of the invention shall be included in the protection scope of the invention.

What is claimed is:

1. A preparation method for Palbociclib (I),

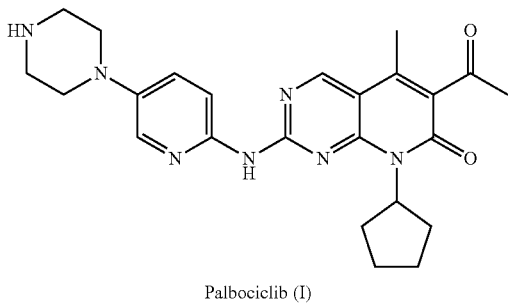 [SMILES: CC(=O)c1c(C)c2cnc(Nc3ccc(N4CCNCC4)cn3)nc2n(C2CCCC2)c1=O]

Palbociclib (I)

the preparation method comprises the steps of: causing a ring-closing reaction of 2-acetyl-2-butenoic acid methyl ester and malononitrile to occur in an alkaline condition to generate 1,4,5,6-tetrahydro-2-methoxyl-4-methyl-5-acetyl-6-oxy-3-pyridine carbonitrile; causing a substitution reaction of 1,4,5,6-tetrahydro-2-methoxyl-4-methyl-5-acetyl-6-oxy-3-pyridine carbonitrile and halogenated cyclopentane to occur under the effect of acid binding agent to generate N-cyclopentyl-1,4,5,6-tetrahydro-2-methoxyl-4-methyl-5-acetyl-6-oxy-3-pyridinecarbonitrile; causing a condensation reaction of N-cyclopentyl-1,4,5,6-tetrahydro-2-methoxyl-4-methyl-5-acetyl-6-oxy-3-pyridinecarbonitrile and N-[5-(1-piperazinyl)-2-pyridinyl]guanidine to occur to generate 6-acetyl-8-cyclopentyl-5,8-dihydro-5-methyl-2-[[5-(1-piperazinyl)-2-pyridinyl]amino]-pyrido[2,3-d]pyrimidin-7(6H)-one; and causing a dehydrogenation reaction of 6-acetyl-8-cyclopentyl-5,8-dihydro-5-methyl-2-[[5-(1-piperazinyl)-2-pyridinyl]amino]-pyrido[2,3-d]pyrimidin-7(6H)-one and sodium selenate to occur to prepare Palbociclib (I).

2. The preparation method for Palbociclib according to claim 1, wherein molar ratio of the aforesaid ring-closing reaction of 2-acetyl-2-butenoic acid methyl ester and malononitrile is 1:0.5-1.5.

3. The preparation method for Palbociclib according to claim 1, wherein alkali required for the aforesaid ring-closing reaction is potassium hydroxide, sodium hydroxide, sodium methoxide, sodium ethoxide, potassium tert-butoxide, sodium tert-butoxide or sodium hydride.

4. The preparation method for Palbociclib according to claim 1, wherein halogen in the raw material halogenated cyclopentane in the aforesaid substitution reaction is fluorine, chlorine, bromine or iodine.

5. The preparation method for Palbociclib according to claim 1, wherein acid binding agent of the aforesaid substitution reaction is triethylamine, pyridine, N-methylmorpholine, diisopropylethylamine, 4-dimethylamino-pyridine, potassium carbonate, lithium carbonate, potassium tert-butoxide or sodium hydride.

6. The preparation method for Palbociclib according to claim 1, wherein molar ratio of the aforesaid condensation reaction of N-cyclopentyl-1,4,5,6-tetrahydro-2-methoxyl-4-methyl-5-acetyl-6-oxy-3-pyridinecarbonitrile and N-[5-(1-piperazinyl)-2-pyridinyl]guanidine is 1:1.0-3.0.

7. The preparation method for Palbociclib according to claim 1, wherein temperature of the aforesaid condensation reaction is 50-150° C.

8. The preparation method for Palbociclib according to claim 1, wherein molar ratio of the aforesaid dehydrogenation reaction of 6-acetyl-8-cyclopentyl-5,8-dihydro-5-methyl-2-[[5-(1-piperazinyl)-2-pyridinyl]amino]-pyrido[2,3-d]pyrimidin-7(6H)-one and sodium selenate is 1:1.0-2.0.

9. The preparation method for Palbociclib according to claim 1, wherein solvent of the aforesaid dehydrogenation reaction is dimethylsulfoxide, and the reaction temperature is 100-180° C.

10. The preparation method for Palbociclib according to claim 1, wherein solvent of the aforesaid substitution reaction of 1,4,5,6-tetrahydro-2-methoxyl-4-methyl-5-acetyl-6-oxy-3-pyridine carbonitrile and halogenated cyclopentane is dichloromethane, chloroform, 1,2-dichloroethane, acetonitrile, methylbenzene, tetrahydrofuran, dimethyl carbonate or dioxane; Solvent of the aforesaid ring-closing reaction of 2-acetyl-2-butenoic acid methyl ester and malononitrile is methanol, ethyl alcohol, isopropyl alcohol or ethylene glycol; Solvent of the aforesaid condensation reaction of N-cyclopentyl-1,4,5,6-tetrahydro-2-methoxyl-4-methyl-5-acetyl-6-oxy-3-pyridinecarbonitrile and N-[5-(1-piperazinyl)-2-pyridinyl]guanidine is methylbenzene, dimethylbenzene, acetic acid, N,N-dimethylformamide, N,N-dimethylacetamide or dimethylsulfoxide.

* * * * *